United States Patent [19]

Heldenbrand

[11] Patent Number: 4,516,431

[45] Date of Patent: May 14, 1985

[54] PIPE TESTING APPARATUS

[76] Inventor: William C. Heldenbrand, P.O. Box 2066, New Iberia, La. 70560

[21] Appl. No.: 508,656

[22] Filed: Jun. 28, 1983

[51] Int. Cl.³ ............................................. G01N 3/08
[52] U.S. Cl. ...................................... 73/826; 73/831
[58] Field of Search ................ 73/826, 831, 834, 837, 73/856

[56]  References Cited

U.S. PATENT DOCUMENTS

| | | | |
|---|---|---|---|
| 2,336,524 | 12/1943 | Bannister | 73/826 |
| 2,757,536 | 8/1956 | Heldenbrand | 73/837 |
| 2,884,986 | 5/1959 | Heldenbrand | 73/831 |
| 3,994,158 | 11/1976 | Weinhold | 73/831 |

*Primary Examiner*—Anthony V. Ciarlante

*Attorney, Agent, or Firm*—Harvey B. Jacobson

[57]  ABSTRACT

A machine is disclosed for applying lengthwise tension to a length of pipe, such as a joint of pipe used in an oil well drill string, for example, for the purpose of testing the pipe for tensile strength. The machine includes gripping assemblies for holding opposite ends of the pipe in respective parts of the machine which are urged apart to apply tension to the pipe. Each gripping assembly includes a rotary mandrel which is threaded onto a sub secured to the respective pipe end, and a header rotatably mounting the mandrel. The header includes a plate providing restraint for the mandrel precluding its expulsion from the machine in the event of a pipe failure during the application of tension thereto. A rotary drive is provided for each mandrel for threading the mandrel onto and off the respective sub.

11 Claims, 5 Drawing Figures

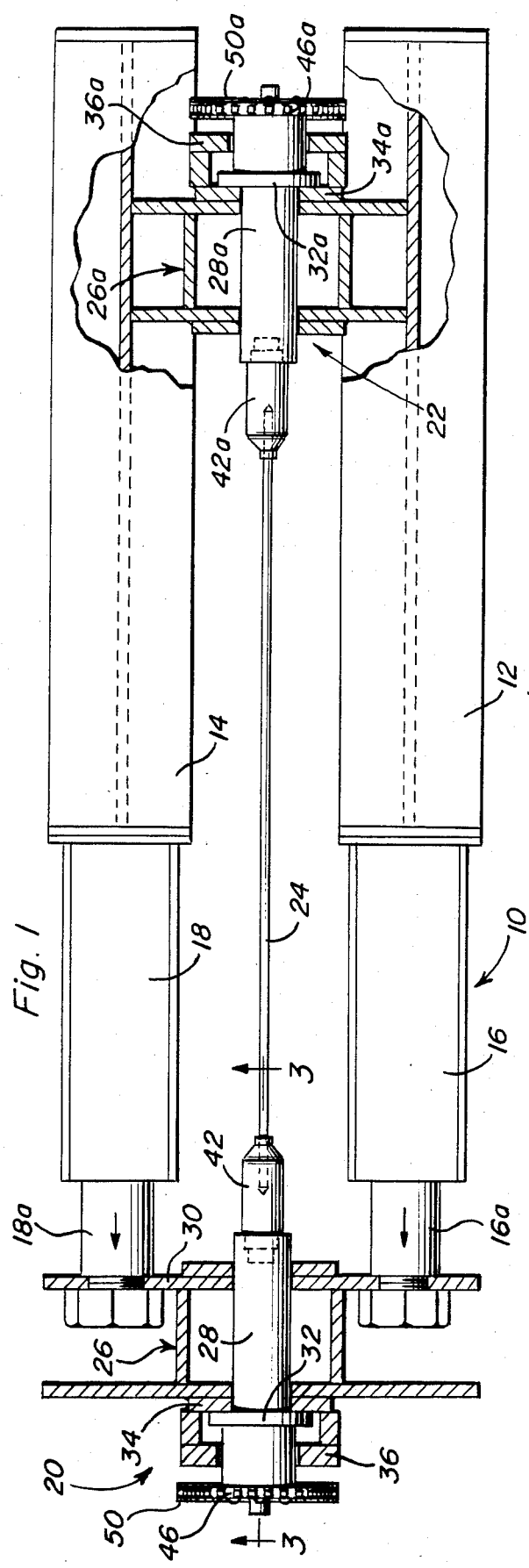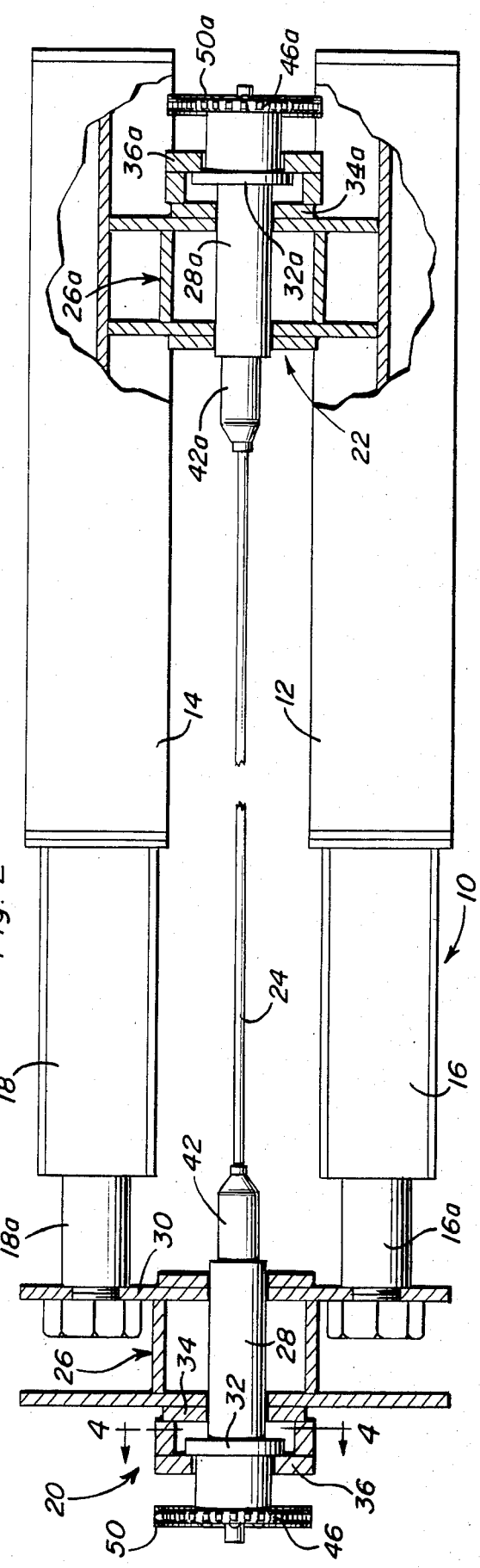

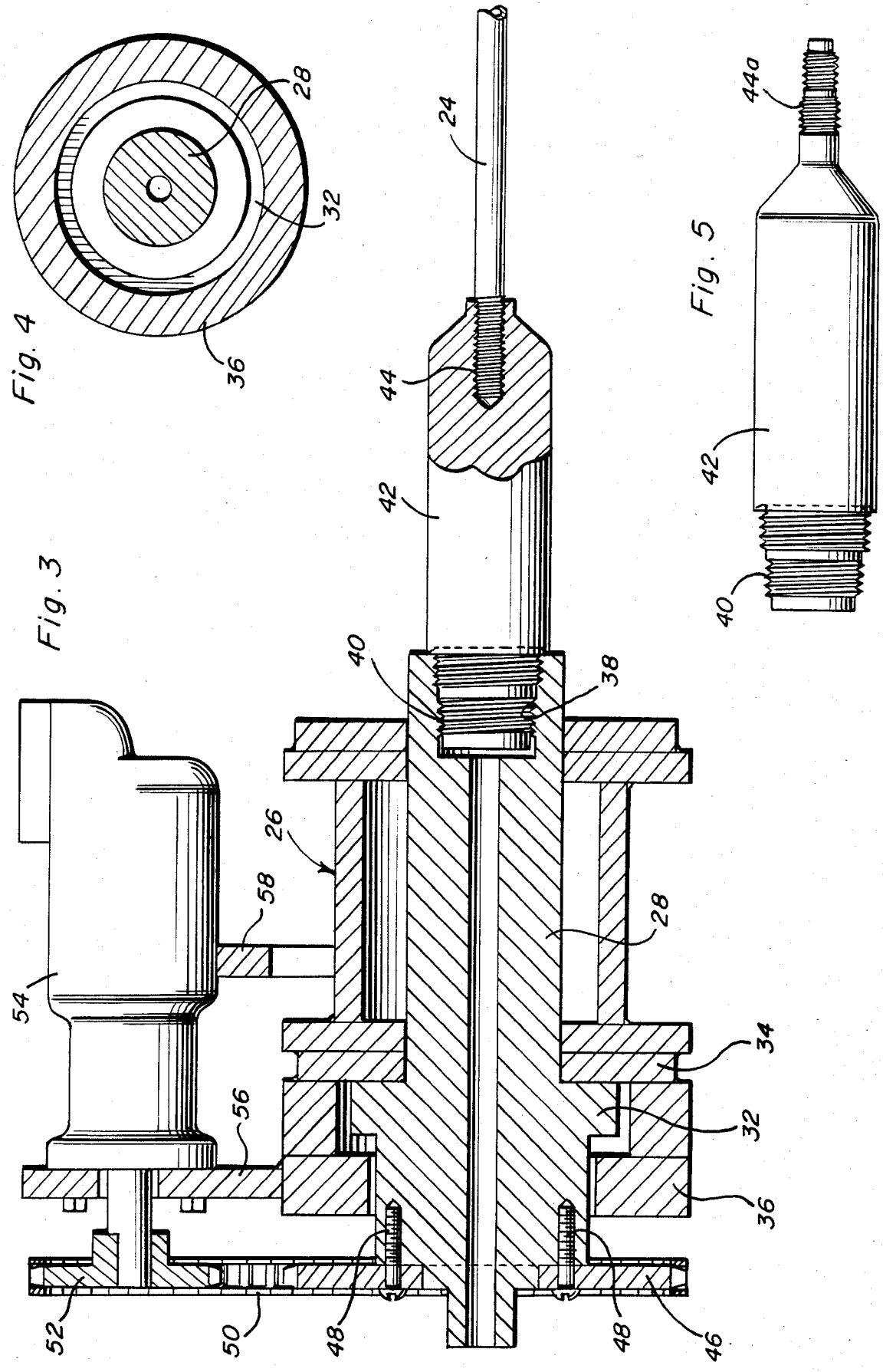

PIPE TESTING APPARATUS

BACKGROUND OF THE INVENTION

This invention relates to apparatus for use in applying tension to lengths of pipe, for example, for testing the tensile strength of joints of pipe used in oil well and like drill strings.

It is well known in the oil industry to test a joint of pipe for strength (or to straighten a pipe length) in a machine which is adapted to apply axial tension to the pipe. A machine of this nature commonly includes elongated beams or the like with hydraulic cylinders at one end. A joint of pipe to be tested is gripped at its opposite ends by gripping assemblies associated with the beams and the hydraulic cylinders respectively so that extension of the cylinders applies axial tension to the pipe.

The forces employed in machines of the above type are considerable, so that should a pipe be defective and rupture under load, the sudden release of tension may cause one or both ends of the pipe to be forcibly expelled from the machine with dangerous consequences. The forces involved can, for example, be of a magnitude to propel part of a ruptured pipe as much as 200 feet.

The present invention provides apparatus for the application of tensile stress to a pipe which includes means for precluding expulsion of a portion of the pipe (and the associated fittings) in the event of a pipe failure resulting in rupture of the pipe during the application of tensile stress thereto.

DESCRIPTION OF THE PRIOR ART

Acknowledgment is made of the following U.S. patents pertaining to apparatus for applying longitudinal tension to elongate members:

| | |
|---|---|
| 2,757,536 | Aug. 2, 1956 |
| 2,884,986 | May 5, 1959 |
| 3,690,160 | Sept. 12, 1972 |
| 3,802,255 | April 9, 1974 |
| 3,994,158 | Nov. 30, 1976 |

SUMMARY OF THE INVENTION

The invention provides apparatus for applying lengthwise tension to joints of pipe for use in drill strings and the like for pipe testing or other purposes, wherein the opposite ends of a joint of pipe or the like are held in gripping assemblies during the application of lengthwise tension to the pipe, the apparatus including means for restraining the respective pipe ends and associated fittings and precluding same from being forcibly expelled from the apparatus in the event of a rupture occurring in the pipe as a result of the application of lengthwise tension thereto.

In a preferred form of the invention, for example, the apparatus may comprise an elongated beam assembly with tension applying hydraulic cylinder means connected at one end thereof, a gripping assembly for one end of a joint of pipe associated with the beam assembly at its opposite end, and a gripping assembly for the other end of the pipe being associated with the cylinder means. Each gripping assembly conveniently may comprise a mandrel for threaded connection to a sub which is secured to the respective pipe end, and a header for mounting the respective mandrel, the headers being connected respectively to the beam assembly and to the hydraulic cylinder means. In order to prevent expulsion of a pipe section, sub and mandrel from the apparatus in the event of a pipe failure as aforesaid, each header may include restraining means for the respective mandrel. For example, the mandrel may include a peripheral flange through which axial tension is applied to the pipe by means of an adjacent shoulder of the header abutting one surface of the flange, and the header may include a further shoulder adjacent the upper surface of the flange forming restraining means for engaging the flange and preventing expulsion of the mandrel and associated pipe section in the event of a sudden release of tension caused by a pipe failure.

In accordance with a further feature of the invention, the mandrels may be rotatably mounted in the respective headers, and drive means, such as a hydraulic motor with a chain and sprocket drive may be associated with each header for applying torque to the respective mandrel in order to thread the mandrel onto or from a sub attached to the end of a pipe to be tested.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a somewhat diagrammatic plan view, partly broken away, of a pipe tensioning apparatus in accordance with the invention.

FIG. 2 is a view similar to FIG. 1 showing various components of the apparatus in positions occupied in the event of a pipe failure under load.

FIG. 3 is a cross-sectional view, to an enlarged scale, on line 3—3 of FIG. 1.

FIG. 4 is a cross-sectional view, to an enlarged scale, on line 4—4 of FIG. 2.

FIG. 5 is an elevational view of a modified form of sub for use in the apparatus.

DESCRIPTION OF THE PREFERRED EMBODIMENT

Referring initially to FIGS. 1 and 2 in particular, there is illustrated a machine 10 for testing pipe lengths such as joints of pipe for use in a drill string for oil well and like drilling, by applying lengthwise tension thereto. Basic components of the machine comprise, in known manner, a pair of elongate beams or the like 12, 14, a pair of hydraulic piston/cylinder assemblies 16, 18, each secured at one end of a respective beam, a first pipe gripping assembly 20 secured to extensible portions (e.g. piston rods 16a, 18a) of the piston/cylinder assemblies, and a second pipe gripping assembly 22 secured to beams 12, 14 adjacent the ends thereof remote from the piston/cylinder assemblies. In use, a length of pipe such as pipe joint 24 may have its opposite ends attached to the respective gripping assemblies (the length of the machine being adapted to the lengths of pipe to be tested) and a measurable amount of lengthwise tension may then be applied to the pipe to test its tensile strength by applying hydraulic pressure to the piston/cylinder assemblies in a manner tending to extend same.

The general configuration and construction of tensile strength testing and like machines of the type described are well known in the art, and accordingly the beam, piston/cylinder assembly structure, and manner of securing the pipe gripping assemblies thereto need not be described in detail. These elements may be of conventional construction. The present invention is particularly concerned with the construction and operation of the pipe gripping assemblies, and with apparatus ancillary thereto, and such assemblies and apparatus will now be described in detail.

Pipe gripping assembly 20 comprises a header 26 and a mandrel 28 rotatably mounted in the header. The header may include a cross piece 30 or the like by which it is secured (through suitable means known in the art) to each of the piston rods 16a and 18a. Mandrel 28 includes a circumferential flange 32 which is located between a pair of plates of header 26, one such plate 34 providing a force applying internal annular shoulder and the other such plate 36 providing an internal annular restraining shoulder. (The header may be initially constructed to include plate 36, or alternatively such plate may be welded to a header on an existing machine to provide a restraining facility, as will be described.)

The inner end of mandrel 28 is recessed (see particularly FIG. 3) and internally threaded at 38 to form a box connection with the externally threaded end 40 of a sub 42, the sub being threaded at its opposite end 44 to one end of pipe 24. End 44 of the sub may be internally threaded as shown in FIG. 4 for receiving an externally threaded pipe end or alternatively the end of sub may be externally threaded as shown at 44a in FIG. 5 to receive an internally threaded pipe end.

The outer end of mandrel 28 carries a sprocket wheel 46 attached thereto by screws 48 or the like, wheel 46 having a chain drive 50 from a drive sprocket 52 of a reversible hydraulic torque motor 54 suitably mounted on the machine, for example, by brackets 56, 58 (See FIG. 3).

Gripping assembly 22 is similar in construction to gripping assembly 20 and like reference numerals (with "a" suffixes) are used to denote like parts therein. Header 26a of assembly 22 is modified compared with header 26 for securement thereof to beams 12 and 14, but the gripping assemblies are alike in other respects. The construction of the machine may be such that header 26a can be releasably secured to the beams in adjusted positions lengthwise of the beams, so that the machine may be adapted for use with different lengths of pipe.

In use, a joint of pipe to be tested may have subs 42, 42a threaded to its opposite ends prior to insertion of the pipe into the machine. Then, mandrels 28, 28a may be suitably rotated by the respective chain and sprocket drives in order to thread the subs into the gripping assemblies thereby securing the pipe in the machine for testing. The pipe may then be tested in tension as previously noted. If a series of pipes with like threaded ends are to be tested in sequence, the subs may be left in the machine after each test and the chain and sprocket drives used, after a test, to unthread the respective mandrels and subs in unison from the respective pipe ends. In these circumstances, the pipe ends should be threaded into the subs with a lower torque than is used in the threaded connection between the subs and the mandrels.

During testing, longitudinal tension is applied to a pipe by means of heater plates 34, 34a abutting and applying tension to the mandrel flanges 32, 32a. Should the applied tension cause the pipe to rupture as shown in FIG. 2, the sudden release of tension will tend to cause the mandrels to be forcibly expelled from the outer ends of the respective headers. However, in such circumstances, flanges 32, 32a will engage plates 36, 36a which provide effective restraining means for the mandrels precluding their expulsion from the machine. The mandrels and headers as described may, for example, be designed to withstand a million pounds of shock force. The drawings are not drawn to scale, and the clearances shown therein may be exaggerated for illustrative purposes. Thus, the amount of mandrel movement, in particular, in the event of a pipe rupture (as shown in FIG. 2) will generally be designed to be accommodated by "play" in the chain and sprocket device.

It will be appreciated from the foregoing that the invention provides a particularly advantageous form of gripping assembly for pipe ends in a tensile pipe testing machine, the assembly employing a header and mandrel arrangement which enables rotation of the mandrel for hydraulic threading of the mandrel onto a pipe end, and which also provides retension of the mandrel preventing expulsion thereof in the event of a pipe failure during testing.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. For a machine used in applying lengthwise tension to a pipe, gripping assemblies for holding the respective pipe ends in respective parts of the machine which are adapted to be urged apart in order to apply tension to the pipe, each gripping assembly including a header means for attachment to the respective part of the machine, a mandrel associated with the header means for attachment to one end of the pipe, abutment means associated with the header means for applying lengthwise force to the mandrel when said parts of the machine are urged apart thereby longitudinally tensioning the pipe, and restraining means associated with the header means for engaging the mandrel and resisting expulsion of the mandrel from the header means in the event of a pipe failure during the application of lengthwise tension thereto, wherein each mandrel has a peripheral projecting means located between respective shoulders of the associated header means, one of said shoulders constituting said abutment means and being adapted to engage one surface of the projecting means for applying lengthwise force to the mandrel, the other of said shoulders constituting said restraining means and being adapted to engage the opposite surface of the projecting means in the event of a pipe failure under tension, thereby precluding expulsion of the mandrel from the header means.

2. The invention of claim 1 wherein each mandrel is mounted in the respective header means for rotation about an axis conforming to the axis of a pipe to be tested, the mandrel having a threaded inner end for threading to a pipe end attachment.

3. The invention of claim 2 including drive means for rotating the mandrel to thread and unthread same to and from the respective pipe end attachment.

4. The invention of claim 3 wherein the drive means includes a driven sprocket on the mandrel, a reversible motor having a drive sprocket, and an endless drive element connecting said sprockets.

5. The invention of claim 1 wherein each mandrel is mounted in a respective header means for rotation about an axis conforming to the axis of a pipe to be tested, the mandrel having a threaded inner end for threading to a pipe end attachment, and drive means for reversibly rotating the mandrel to thread same onto and off the pipe end attachment, the drive means including a sprocket connected to the mandrel outwardly of said shoulders and means for applying reverse rotation to the sprocket.

6. The invention of claim 5 including a pipe end attachment in the form of a sub threaded to the inner end of the mandrel, the sub itself being threaded to receive a threaded pipe end.

7. The invention of claim 6 including a pipe threaded to the sub with less torque than the torque with which the sub is threaded to the mandrel.

8. The invention of claim 1 wherein the peripheral projecting means is a circumferential flange.

9. A machine for use in applying lengthwise tension to a pipe for pipe testing and the like, the machine comprising gripping assemblies for the pipe ends for holding the pipe ends in respective parts of the machine which are adapted to be urged apart in order to apply lengthwise tension to the pipe, each gripping assembly including a header means attached to a respective one of said parts of the machine, and a mandrel associated with the header means, the mandrel being mounted in the header means for rotation about an axis conforming to the longitudinal axis of a pipe to be tensioned, and the mandrel having a threaded inner end for threading to a pipe end attachment, wherein each mandrel includes a peripheral flange located between a pair of internal shoulders provided in the respective header means, an inner one of said shoulders providing means for applying outwardly directed force to the mandrel for tensioning a pipe by engagement against one surface of the flange, and the outer one of said shoulders constituting restraining means adapted to engage the other surface of the flange in the event of a pipe failure during the application of tension thereto, so as preclude expulsion of the mandrel from the header means.

10. A machine as claimed in claim 9 including drive means for rotating the mandrel to thread and unthread same to and from the respective pipe end attachment.

11. A machine as claimed in claim 10 wherein the drive means includes a driven sprocket on the mandrel, a reversible motor having a drive sprocket, and an endless drive element connecting said sprockets.

* * * * *